United States Patent
Obeng

(10) Patent No.: US 6,684,704 B1
(45) Date of Patent: Feb. 3, 2004

(54) MEASURING THE SURFACE PROPERTIES OF POLISHING PADS USING ULTRASONIC REFLECTANCE

(75) Inventor: Yaw S. Obeng, Orlando, FL (US)

(73) Assignee: PsiloQuest, Inc., Orlando, FL (US)

( * ) Notice: Subject to any disclaimer, the term of this patent is extended or adjusted under 35 U.S.C. 154(b) by 0 days.

(21) Appl. No.: 10/241,985

(22) Filed: Sep. 12, 2002

(51) Int. Cl.⁷ .......................... G01N 29/10; B24B 49/00
(52) U.S. Cl. ........................ 73/602; 73/628; 73/629; 73/648; 451/6; 451/21
(58) Field of Search .................. 451/5, 6, 8, 9, 451/10, 21, 28, 41, 56, 54, 287, 288, 165; 73/597, 432.1, 598, 599, 600, 602, 627, 628, 629, 645, 646–648

(56) References Cited

U.S. PATENT DOCUMENTS

| | | | |
|---|---|---|---|
| 4,168,353 A | | 9/1979 | Kitamori |
| 4,272,924 A | * | 6/1981 | Masuko et al. ............... 451/1 |
| 4,703,656 A | | 11/1987 | Bhardwaj |
| 5,332,943 A | | 7/1994 | Bhardwaj |
| 5,578,362 A | | 11/1996 | Reinhardt et al. |
| 5,624,303 A | | 4/1997 | Robinson |
| 6,045,434 A | * | 4/2000 | Fisher, Jr. et al. ............ 451/6 |
| 6,051,500 A | | 4/2000 | Maury et al. ............... 438/692 |
| 6,099,954 A | | 8/2000 | Urbanavage et al. |
| 6,264,532 B1 | * | 7/2001 | Meloni ........................... 451/6 |
| 6,267,644 B1 | | 7/2001 | Molnar |
| 6,283,829 B1 | | 9/2001 | Molnar |
| 6,291,349 B1 | | 9/2001 | Molnar |
| 6,293,851 B1 | | 9/2001 | Molnar |
| 6,300,386 B1 | | 10/2001 | Karukaya et al. |
| 6,311,573 B1 | | 11/2001 | Bhardwaj |
| 6,328,634 B1 | | 12/2001 | Shen et al. |
| 6,343,510 B1 | | 2/2002 | Neeson et al. |
| 6,346,202 B1 | | 2/2002 | Molnar |
| 6,354,915 B1 | | 3/2002 | James et al. |
| 6,413,153 B1 | | 7/2002 | Molar |
| 6,419,556 B1 | | 7/2002 | Urbanavage et al. |
| 6,425,803 B1 | | 7/2002 | Baker, III |
| 6,425,816 B1 | | 7/2002 | Roberts et al. |
| 6,428,388 B2 | | 8/2002 | Molnar |
| 6,435,948 B1 | | 8/2002 | Molnar |
| 6,585,574 B1 | | 7/2003 | Lombardo et al. .......... 451/285 |

FOREIGN PATENT DOCUMENTS

WO     WO 99/10129     3/1999

OTHER PUBLICATIONS

David G. Totzke; "Ultrasound Diagnostic of Chemical Mechanical Planarization Pads"; Aug. 2000; p. 1–62.

Encyclopedia of Smart Materials, 2 Volume Set; Mar. 2002.

D.G. Totzke, A. Belyaev, W. Moreno, S. Ostapenko, I. Tarasov, W. Easter, A. Maury, and A. Crevasse; Non–Destructive Characterization of CMP Pads Using Scanning Ultrasonic Transmission; AIP Conference Proceedings, American Institute of Physics, 1970. pp. 259–262.

M.A. Rodriguez–Perez, A. Duijsens and J.A. De Saja; "Effect of Addition of EVA on the Technical Properties of Extruded Foam Profiles of Low–Density Polyethylene/EVA Blends"; Effects of Eva on Properties of LDPE/EVA Blends; Oct. 1997; pp. 1237–1244.

* cited by examiner

Primary Examiner—Hezron Williams
Assistant Examiner—Rose M. Miller

(57) ABSTRACT

The present invention provides a system and method for measuring the surface properties of polishing pads using noncontact ultrasonic reflectance. An ultrasonic probe is located over the polishing surface and configured to both transmit an ultrasonic signal to the polishing surface and receive a modified ultrasonic signal from the polishing surface without contacting the polishing surface. A subsystem coupled to the ultrasonic probe is configured to determine a surface property of the polishing pad from the modified signal.

10 Claims, 15 Drawing Sheets

MEASURING THE SURFACE PROPERTIES OF POLISHING PADS USING ULTRASONIC REFLECTANCE

CROSS-REFERENCE TO RELATED APPLICATIONS

This application is an improvement upon that disclosed of U.S. application Ser. No. 10/000,101, entitled, "THE SELECTIVE CHEMICAL-MECHANICAL POLISHING PROPERTIES OF A CROSS LINKED POLYMER AND SPECIFIC APPLICATIONS THEREFOR," to Yaw S. Obeng and Edward M. Yokley, filed on Oct. 24, 2001, U.S. application Ser. No. 09/998,471, entitled, "A METHOD OF INTRODUCING ORGANIC AND INORGANIC GRAFTED COMPOUNDS THROUGHOUT A THERMOPLASTIC POLISHING PAD USING A SUPERCRITICAL FLUID AND APPLICATIONS THEREFOR," to Edward M. Yokley and Yaw S. Obeng, filed on Nov. 29, 2001, and U.S. application Ser. No. 10/241,074, entitled, "A POLISHING PAD SUPPORT THAT IMPROVES POLISHING PERFORMANCE AND LONGEVITY," to Yaw S. Obeng and Peter Thomas filed on Sep. 11, 2002, which are commonly assigned with the present invention, and incorporated by reference as if reproduced herein in their entirety.

TECHNICAL FIELD OF THE INVENTION

The present invention is directed to a system and method of measuring the surface properties of chemical mechanical polishing pads used for creating a smooth, ultra-flat surface on such items as glass, semiconductors, dielectric/metal composites, magnetic mass storage media and integrated circuits. More specifically, the invention is directed to the use of noncontact reflectance ultrasound to measure the surface coating and wearing patterns of polishing pads.

BACKGROUND OF THE INVENTION

Chemical-mechanical polishing (CMP) is used extensively as a planarizing technique in the manufacture of Very Large-Scale Integration (VLSI) integrated circuits. It has potential for planarizing a variety of materials in IC processing, but is used most widely for planarizing metallized layers and interlevel dielectrics on semiconductor wafers, and for planarizing substrates for shallow trench isolation.

The growing use of copper for circuit interconnects, but lack of etching techniques to remove copper, has led to the adoption of damascene processes and the use of CMP to remove excess copper and associated barrier metals. In shallow trench isolation, for example, large areas of field oxide must be polished via to produce a planar starting wafer. Achieving acceptable planarization across the full diameter of a wafer using traditional etching processes has been largely unsuccessful. However, using conventional CMP, where the wafer is polished using a mechanical polishing wheel and a slurry of chemical etchant, unwanted oxide material is removed with a high degree of planarity.

Similarly, multilevel metallization processes, each level in the multilevel structure contributes to irregular topography. Planarizing interlevel dielectric layers, as the process proceeds, is often now favored in many state-of-the-art IC fabrication processes. High levels of planarity in the metal layers is a common objective, and this is promoted by using plug interlevel connections. A preferred approach to plug formation is to blanket deposit a thick metal layer, comprising, for example W, Ti, TiN, on the interlevel dielectric and into interlevel windows, and then removing the excess metal using CMP. CMP may also be used for polishing an oxide layers, such as $SiO_2$, $Ta_2O_5$ or $W_2O_5$ or to polish nitride layers such as $Si_3 N_4$, TaN, TiN.

There are, however, deficiencies in our understanding the multiple factors that affect CMP performance. These deficiencies derive in part from the lack to nondestructive methods to evaluate efficacy of steps in the production CMP pads, as well as evaluating the wearing characteristics of such pads. For example, the mechanical and chemical properties of CMP pads may be evaluated by dynamic mechanical analysis (DMA) and Fourier Transform Infrared (FTIR) Spectroscopy, respectively. Such measurements, however are performed on strips or samples of material cut from pads. These approaches, therefore, are not ideally suited to provide information about the dynamics of pad production and wear during use. Ultrasound provides a potential means to nondestructively evaluate these properties.

Noncontact optoacoustic metrology, for example, using laser light to generate and detect ultrasonic waves, has been used to characterize metal deposition and uniformity on semiconductor wafers before and after CMP. Techniques that bounce an acoustic signal off of the wafer being polished, similar to sonar principles, have been used to detect polishing end points. Direct transmission scanning ultrasound, where an ultrasonic signal generated by a transducer attached to a pad is passed through the pad to a receiver on the opposite side of the pad, has been used to detect inhomogeneities in ultrasonic transmission amplitudes, possibly related to the pad's density, elastic modulus or viscosity coefficient. This approach, however, requires intimate contact between the measuring device and the material being tested, either by immersing the material in a coupling fluid or by vacuum suction of a sensor to the material's surface. Such contact disturbs the surface that is being measured. Such measurement approaches are also un acceptably slow, for example, requiring more than one day to measure the surface of a polishing pad. Moreover, none of the above described approaches, address inspecting of pad surfaces during their production and monitoring the pad's wear characteristics.

Accordingly, what is needed is an improved method of using ultrasound to nondestructively monitor the production and wearing patterns of the surface of CMP pads, while not experiencing the above-mentioned problems.

SUMMARY OF THE INVENTION

To address the above-discussed deficiencies, the present invention provides, in one embodiment, a system for measuring surface properties of a polishing pad. The system comprises a polishing pad having a polishing surface associated therewith, an ultrasonic probe located over the polishing surface and a subsystem coupled to the ultrasonic probe. The probe is configured to both transmit an ultrasonic signal to the polishing surface and receive a modified ultrasonic signal from the polishing surface without contacting the polishing surface. The subsystem is configured to determine a surface property of the polishing pad from the reflection.

In yet another embodiment, the present invention provides a method for measuring the surface properties of a polishing pad. The method includes situating an ultrasonic probe above a polishing surface of a polishing pad, without contacting the polishing surface. The method further comprises transmitting an ultrasonic signal from the probe to the polishing surface, the ultrasonic signal being modified by the polishing surface. The method also includes receiving the modified signal by the ultrasonic probe.

The foregoing has outlined preferred and alternative features of the present invention so that those skilled in the art may better understand the detailed description of the invention that follows. Additional features of the invention will be described hereinafter that form the subject of the claims of the invention. Those skilled in the art should appreciate that they can readily use the disclosed conception and specific embodiments as a basis for designing or modifying other structures for carrying out the same purposes of the present invention. Those skilled in the art should also realize that such equivalent constructions do not depart from the scope of the invention.

BRIEF DESCRIPTION OF THE DRAWINGS

For a more complete understanding of the invention, reference is now made to the following descriptions taken in conjunction with the accompanying drawing, in which.

DETAILED DESCRIPTION

Recently, ultrasonic transducers have been developed to facilitate the transmitting and receiving of ultrasonic signals through air to perform noncontact testing of paper, wood, ceramics, metals, plastics and composites. The present invention exploits the previously unrecognized advantages of using a system incorporating such transducers and associated instrumentation, and using a method to measure the surface properties of polishing pads. This approach is superior to previous approaches that required making intimate contact between sensors and the sample surface being measured. In particular, the system and method of the present invention may be advantageously used to monitor the production of pads, in particular the coating or impregnation of such pads with ceramic materials. The system and method may also be beneficially used to observe the wear patterns of the polishing surfaces of such pads after periods of use.

Figure 1:
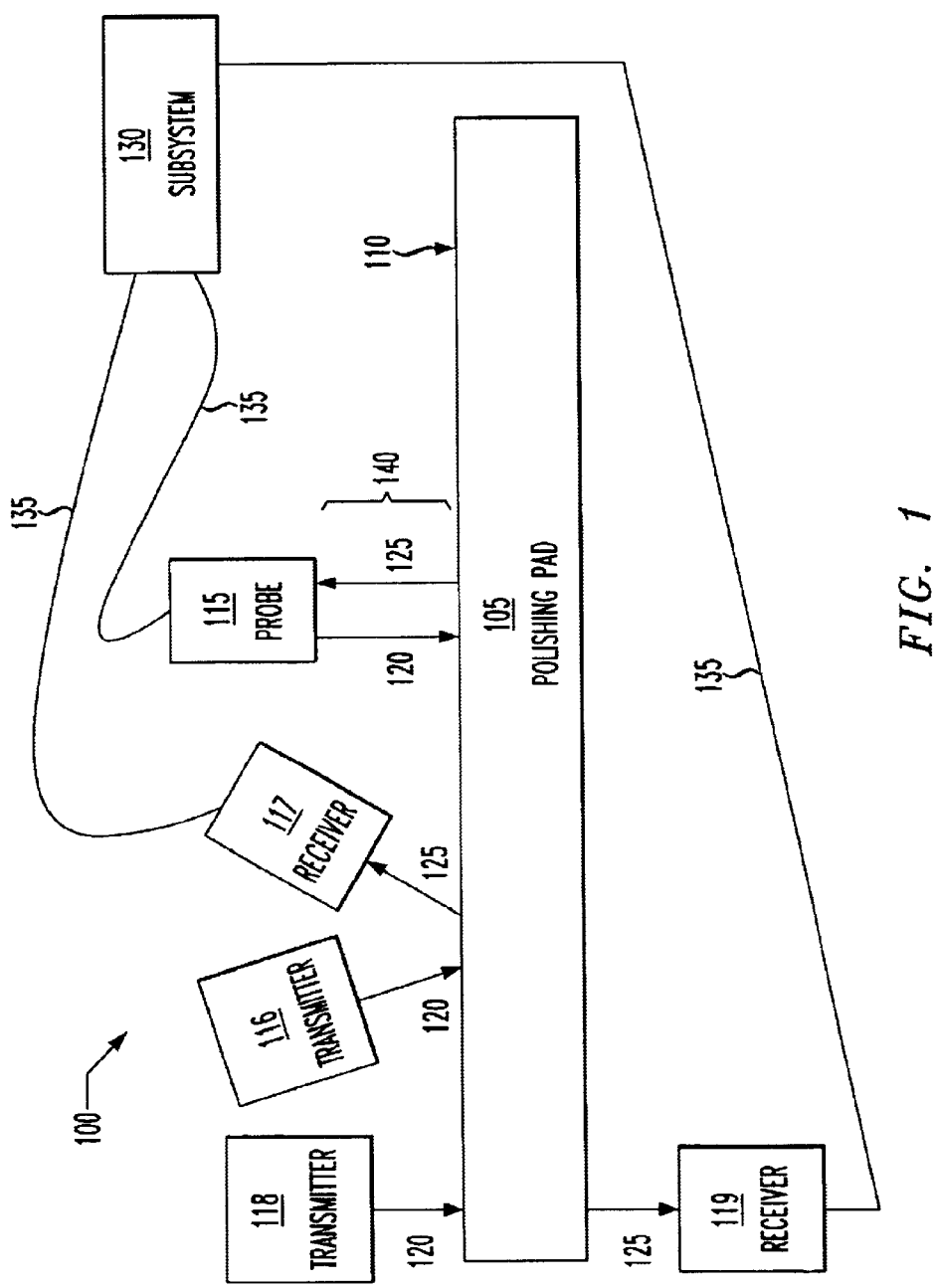
FIG. 1 illustrates a system for measuring surface properties of a polishing pad.

FIG. 1 illustrates one embodiment of the present invention, a system 100 for measuring surface properties of a polishing pad. The system 100 comprises a polishing pad 105 having a polishing surface 110 associated therewith. The system also has an ultrasonic probe 115 located over the polishing surface 110. The probe 115 transmits an ultrasonic signal 120 to the polishing surface, and receives a modified ultrasonic signal 125 from the polishing surface 110 without contacting the polishing surface 110. The system 100 also includes a subsystem 130 coupled to the ultrasonic probe 115 and configured to determine a surface property of the polishing pad 105 from the modified signal 125.

The subsystem 130 may be coupled to the probe 115 via a conventional data communication line 135 or via a conventional wireless communication means. The ultrasonic probe 115 preferably comprises a single ultrasonic transducer. In alternative embodiments, however, the probe 115 may comprise a separate ultrasonic transducers configured for transmitting and receiving. Exemplary designs for the probe 115, subsystem 130 and communication line 135 are presented in U.S. Pat. No. 6,311,573 to Bhardwaj, and U.S. Pat. No. 6,343,510 to Neeson et al., both incorporated herein by reference.

In certain embodiments, for example, the probe 115 comprises separate first and ultrasonic transducers configured as a transmitter and receiver 116, 117. The transmitter and receiver 116, 117 are located above the surface 110 such that the transmitted 120 and received 125 signals are not perpendicular to the surface 110. In still other embodiments, the probe 115 comprises a first ultrasonic transducers configured transmitter 118, on the same side as the surface 110, which generates a transmitted signal 120 that goes through the entire pad 105, thereby providing a signal 125 to a second ultrasonic transducers configured as a receiver 119 located on the opposite side of the pad 105. Combinations of different probe 115 configurations may be advantageously used to provide multiple measurements of a polishing pad.

As further illustrated in the Experimental section to follow, the probe's 115 ultrasonic signal 120 transmission frequency and the air gap 140 located between polishing surface 110 and the probe 115, are important parameters affecting the utility of the reflected signal 125. In certain embodiments, for example, the transmitted ultrasonic signal 120 is between about 100 kHz and about 5 MHz, and more preferably between about 2 MHz and about 3 MHz. The air gap 140 is between about 5 mm and about 50 mm and more preferably between about 12 mm and about 25 mm. In certain preferred embodiments, the transmitted ultrasonic signal 120 is about 3 MHz and the air gap 140 is about 12.5 mm.

The polishing pad 105 and polishing surface 110 may comprise any conventional material used for CMP. More preferably, the pad 105 and polishing surface 110 are any of the materials described in any of the above references patent applications by Obeng and Yokley; Yokley and Obeng; or Obeng and Thomas. For example, the polishing pad may comprise a thermoplastic foam substrate and a polishing agent coating the polishing surface of the substrate. In certain preferred embodiments, the thermoplastic foam substrate comprises a crosslinked polyethylene closed-cell foam. In other preferred embodiments the polishing agent is selected from a group of ceramics consisting of Silicon Dioxide, Titanium Dioxide, Tetraethoxy Silane Polymer and Titanium Alkoxide Polymer. In other advantageous embodiments, the polishing agent is selected from a group of polymers consisting of Polyalcohols; and Polyamines.

The system 100 may be used to characterize any number of surface properties of the polishing surface 110 may be determined from the reflected signal 125 using methods well known to one of ordinary skill in the art. Non-limiting examples include Density, Surface Texture and Visco-Elasticity. However, any of the properties discussed in Mahesh C. Bhardwaj, Non-Contact Ultrasound: The Last Frontier in Non-Destructive Testing and Evaluation, in ENCYCLOPEDIA OF SMART MATERIALS (Mel Swartz ed., 2002), incorporated herein by reference, may be determined.

Figure 2:
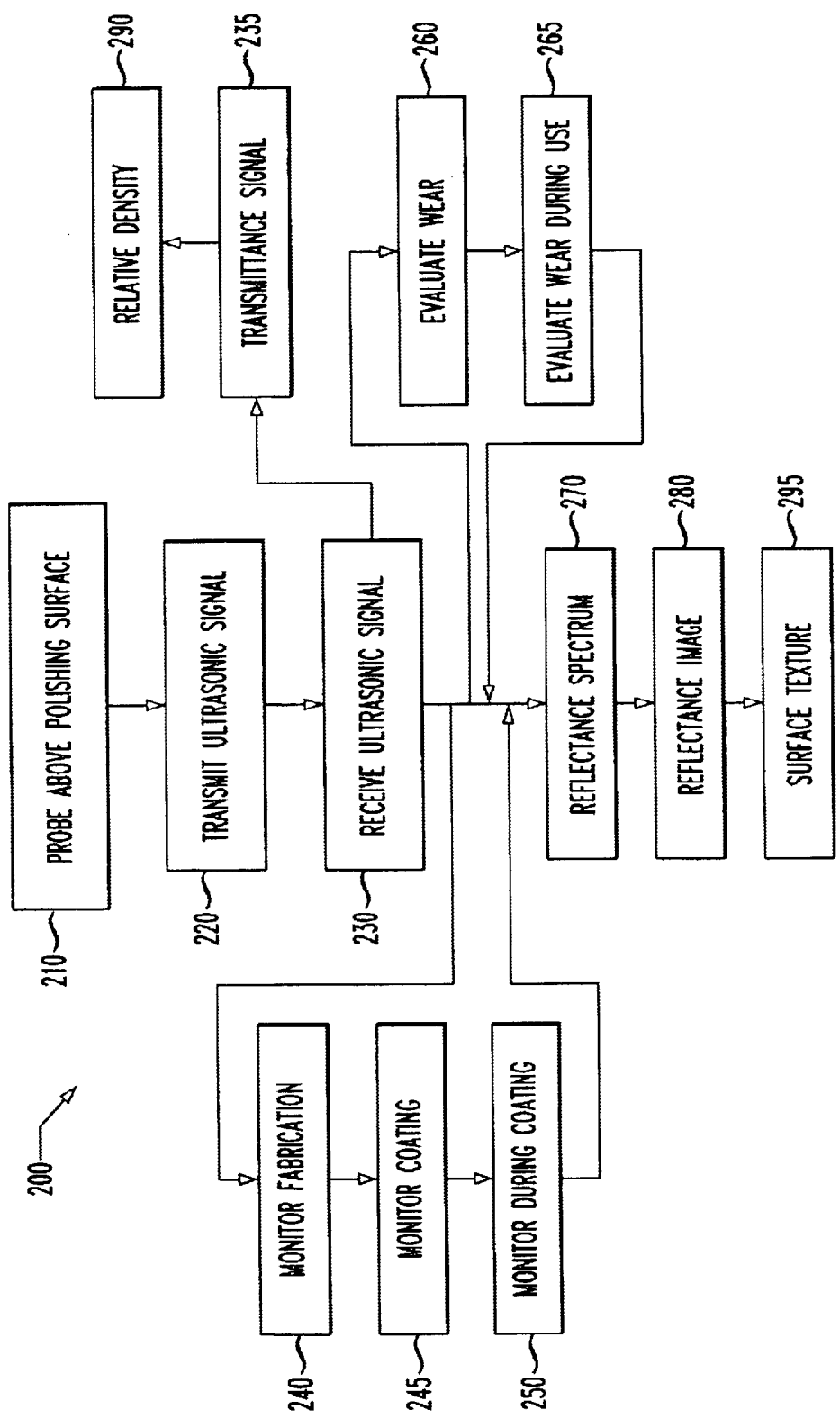
FIG. 2 illustrates, by flow diagram, a method for measuring surface properties of a polishing pad.

Yet another embodiment of the present invention is a method for measuring the surface properties of a polishing pad. Turning to the flow diagram depicted in FIG. 2, the method 200 includes situating an ultrasonic probe above a polishing surface of a polishing pad 210, without contacting the polishing surface. The method 200 further includes transmitting an ultrasonic signal 220 from the probe to the polishing surface, the ultrasonic signal being modified by the polishing surface. The method 200 also includes receiving the modified signal 230 reflected from the polishing surface by the same or different ultrasonic probe. In certain alternative embodiments, where separate ultransonic probes configured as transmitter and receiver are configured in different locations at a non-perpendicular angles above the surface above or on either side of the pad, receiving the signal 230 further includes receiving a transmittance signal 235 transmitted by the transmitter through the pad or reflected from the transmitter to a receiver.

In certain embodiments, the method 200 may be advantageously used to monitor the fabrication 240 of any conventional polishing pad. The method 200 may be incorporated into any of the procedures described in the above cited patent applications for the production of polishing pads. In particular, the method 200 may be advantageously used for monitoring the coating of a polishing agent 245 onto the polishing surface of a thermoplastic foam substrate. Monitoring 245 may be done, for example, by transmitting and receiving 220, 230 ultrasonic signals after a period of coating the polishing pad.

In certain preferred embodiments, however, the monitoring is performed during the coating process 250, with the probe and the polishing pad located in a reaction chamber used for coating. In certain embodiments, for example, the coating process may comprise exposing a surface of the thermoplastic foam substrate to an initial plasma reactant to produce a modified surface thereon. The modified surface is then exposed to a secondary plasma reactant to create the polishing surface on the modified surface, the polishing surface comprised of the polishing agent. Alternatively, the coating process may include exposing a plastic substrate to a polishing agent dissolved in a supercritical fluid to thereby produce a modified plastic.

In other preferred embodiments, the method 200 may be advantageously used to evaluate the wear pattern 260 of any conventional polishing pad after a period of use to polishing a wafer, such as a semiconductor wafer. In certain preferred embodiments, however, the method 200 is used to evaluate the wearing of a polishing pad during polishing 265. In such embodiments, the polishing pad and the probe are coupled to a polishing apparatus comprised of a mechanically driven carrier head and a polishing platen. For example, the polishing pad is attached to the polishing platen and the transmitting and receiving 220, 230 are carried out while the carrier head holds a wafer and imparts a polishing force against the polishing pad to polish a wafer.

The method 200 may include any conventional signal processing steps to convert the reflected signal 230 into information about the surface properties of the polishing pad. For example, the reflected signal 230 may be used to calculate an acoustic reflectance spectrum 270 of the polishing surface. The reflected signal 230 may be rasterized to produce an acoustic reflectance image 280 of the polishing surface. Similarly, the reflected signal 230 may be used to determine a surface texture of the polishing surface 290. Alternatively, in certain embodiments, the transmittance signal 235 may be used to determine a relative density 295 of the polishing surface.

Having described the present invention, it is believed that the same will become even more apparent by reference to the following experiments. It will be appreciated that the experiments are presented solely for the purpose of illustration and should not be construed as limiting the invention. For example, although the experiments described below may be carried out in a laboratory setting, one skilled in the art could adjust specific numbers, dimensions and quantities up to appropriate values for a full-scale plant setting.

EXPERIMENTS

Two sets of experiments were conducted to examine the use of noncontact ultrasound to: 1) monitor the coating of thermoplastic substrates with polishing agents; and 2) evaluate the wearing pattern of polishing surfaces of polishing pads after various periods of use.

Experiment 1

A thermoplastic foam substrate was formed into circular polishing pads of approximately 120 cm diameter of about 0.3 cm thickness. The commercially obtained thermoplastic foam substrate (J-foam from JMS Plastics, Neptune N.J.), designated as "J-60," comprised a blend of about 18% EVA, about 16 to about 20% talc, and balance polyethylene and other additives, such as silicates, present in the commercially provided substrate. The J-60 sheets were skived with a commercial cutting blade (Model number D5100 K1, from Fecken-Kirfel, Aachen, Germany). The sheets were then manually cleaned with an aqueous/isopropyl alcohol solution.

The J-60 substrate was then coated with a polishing agent comprising Tetraethoxy Silane (TEOS), by placing the skived substrate into a reaction chamber of a conventional commercial Radio Frequency Glow Discharge (RFGD) plasma reactor having a temperature controlled electrode configuration (Model PE-2; Advanced Energy Systems, Medford, N.Y.). The plasma treatment of the substrate was commenced by introducing the primary plasma reactant, Argon, for 30 seconds within the reaction chamber maintained at 350 mTorr. The electrode temperature was maintained at 30° C., and a RF operating power of 300 Watts was used. Subsequently, the secondary reactant was introduced for periods ranging from about 0 to about 45 minutes at 0.10 SLM and consisted of TEOS mixed with He or Ar gas. The amount of secondary reactant in the gas stream was governed by the vapor back pressure (BP) of the secondary reactant monomer at the monomer reservoir temperature (MRT; 50±10° C.).

Figure 3:
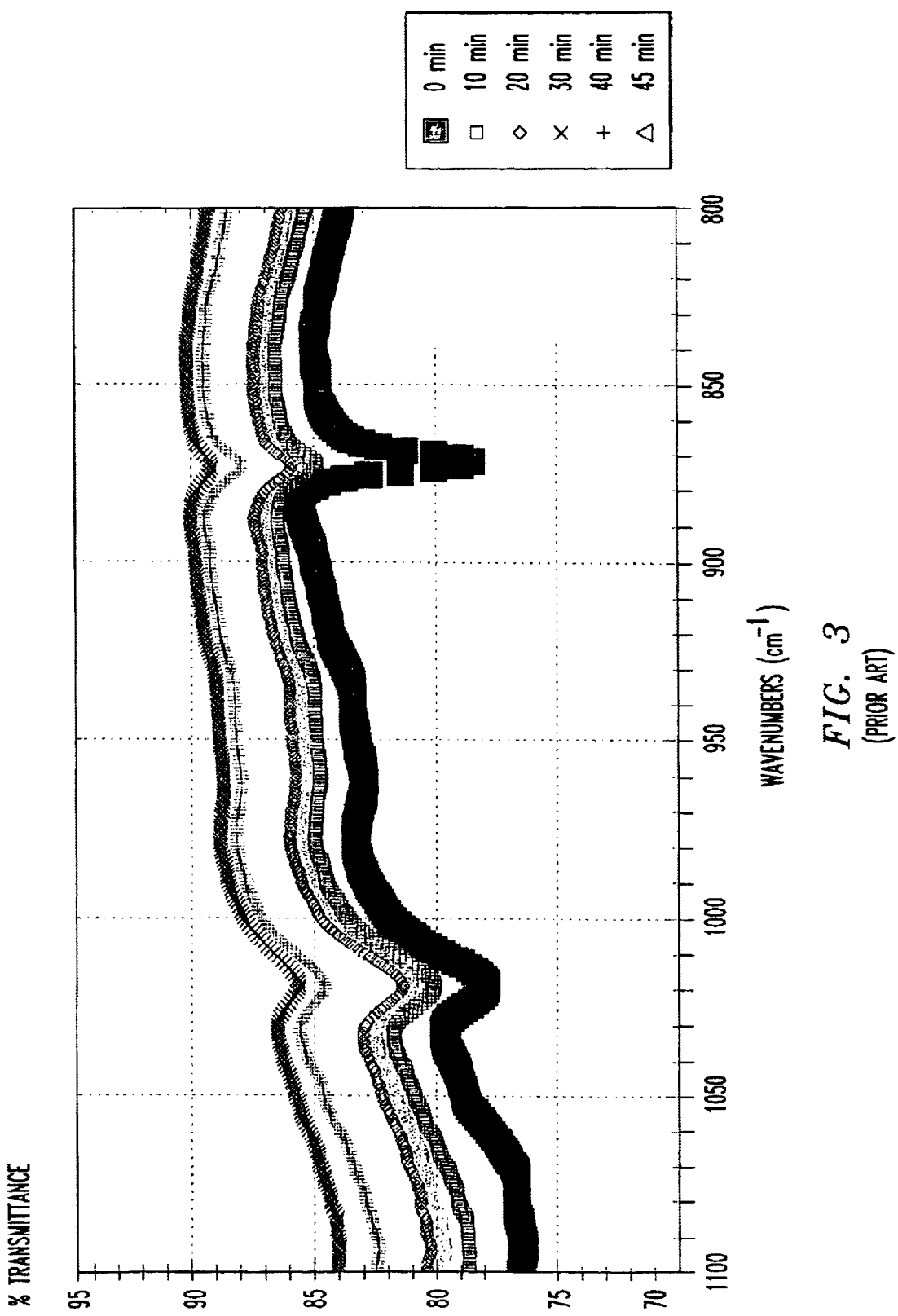
FIG. 3 presents representative near infrared spectra of samples of different thermoplastic foam polishing pads after variable periods of coating with a polishing agent comprising Tetraethoxy Silane (TEOS)
Figure 4:
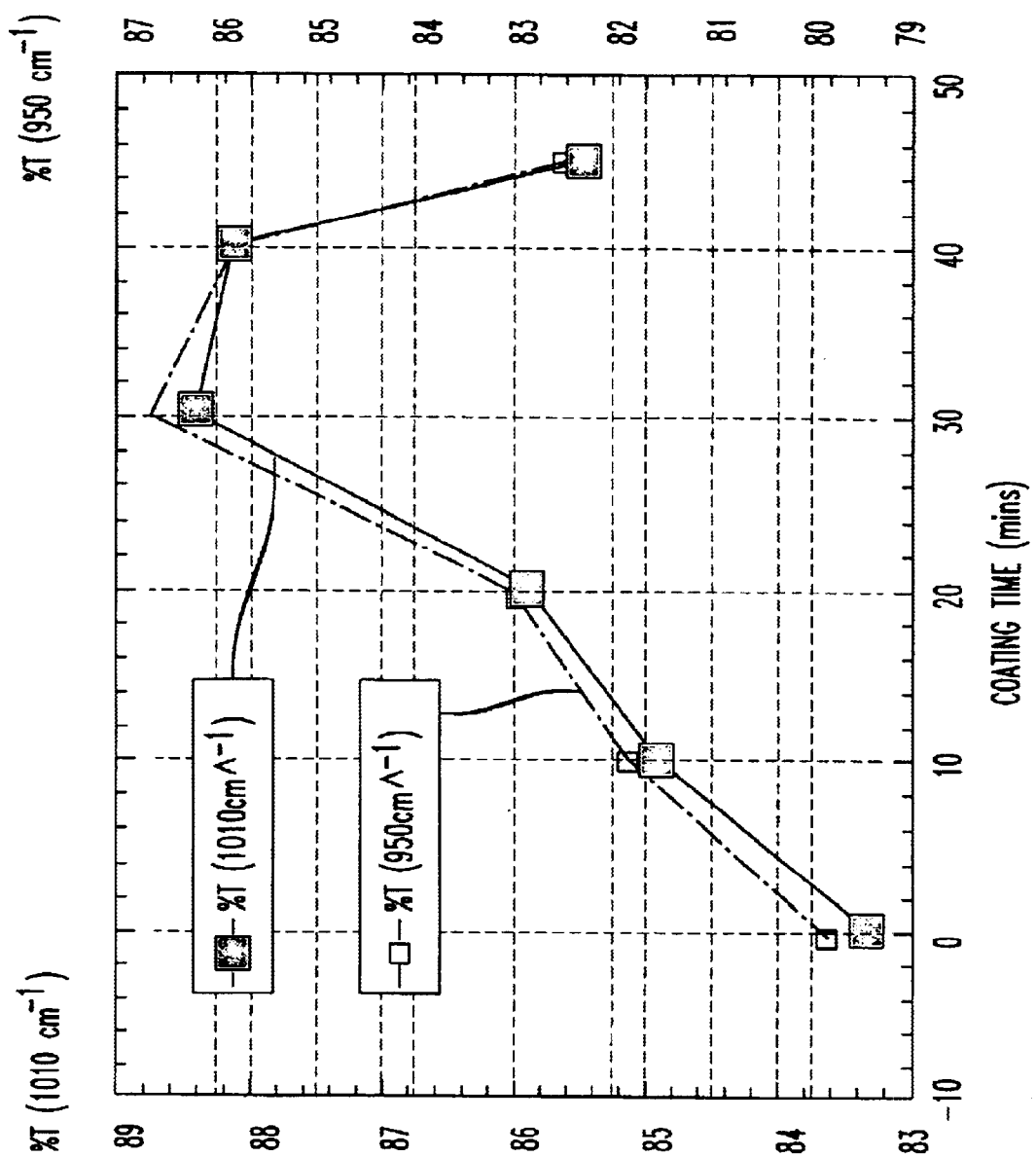
FIG. 4 shows the change in near infrared signal for representative thermoplastic foam polishing pads exposed to different coating periods with TEOS.

FIGS. 3 and 4 illustrate the use of a conventional process, FTIR spectroscopy, to monitor the coating of the substrate's polishing surface with the TEOS polishing agent. Spectra were obtained on a FTIR spectrometer (FTIR 1727, Perkin-Elmer). Samples of the substrate after different periods of coating were removed from the reaction chamber and prepared for FTIR spectroscopy. This illustrates at least two limitations in using FTIR spectroscopy to monitor the coating process: multiple pads must be sacrificed and multiple samples must be obtained during the coating process, thus requiring the process to be stopped at different intervals to obtain the sample.

FIG. 3 illustrates that as coating time increases, the FTIR spectroscopy signals at about 1010 (assigned to Si—O—Si strech) and about 850 $cm^{-1}$ (assigned to Si—OH) decreased, due to net accumulation of silicates on the pad surface. As illustrated in FIG. 4, the transmittance at either wavenumber increases linearly from 0 to 30 min and then starts to decrease thereafter. The decrease in transmittance is thought to be due to competitive signals being received from native versus deposited silicates. As noted above, the foams pads also contain silicates as filler material. These native silicates have essentially the same FTIR signature as the deposited silicates from TEOS. The deposition process involves both sputtering off the surface native silicates and deposition of silicates via plasma enhanced chemical vapor deposition (CVD). After about 30 mins deposition, the native silicate is substantially replaced or covered by the deposited silicates. This will result in FTIR signals primarily from the deposited silicates, which is thought to have slightly different optical characteristics from the native silicate. This illustrates yet another limitation in using FTIR spectroscopy to monitor the coating process: distinguishing between silicate native to the pad material versus deposited silicates.

FIG. 5 illustrates the use of noncontact reflectance ultrasound to monitor the coating or polishing pads, according to the present invention. The transducer and associated subsystem components are commercially available (SecondWave Systems, Boalsburg, Pa.). For the results shown in FIG. 5, the polishing surface of J60 substrates were coated using a process similar to that described above, using a polishing agent comprising silicon dioxide. The reflectivity of the polishing surface was measured on different polishing pads removed from the reaction chamber after different periods of coating. It is important to note, however, that once the optimal measurement conditions had been established, the reflectivity of a single polishing pad could have been monitored continuously during the coating process. One skilled in the art would understand that these measurements are sensitive to the distance of the transducer from the surface of the pad, and that the distance must be routinely optimized for maximum sensitivity and reproducibility.

Figure 5A:
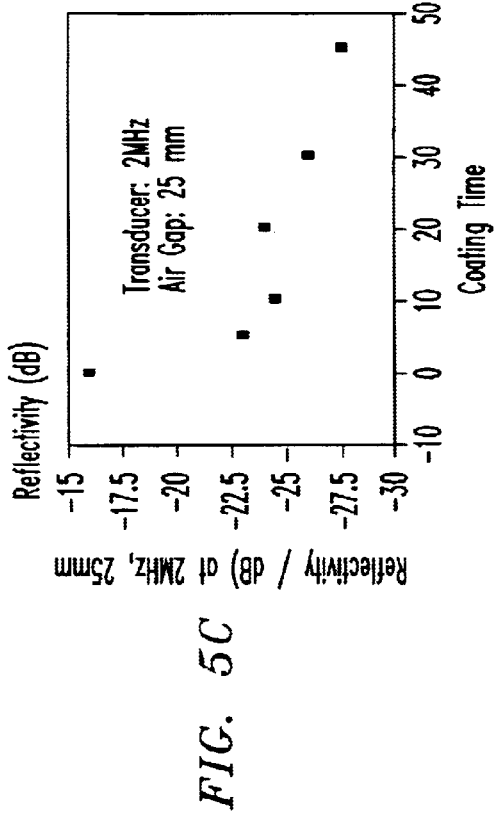
FIG. 5 shows the time course in change in the acoustic reflectance from the surface of exemplary polishing pads as a function of silicon dioxide coating time and illustrates the relationship between acoustic reflectance, transducer transmission frequency and the air gap between the transducer and the polishing pad surface being coated with a polishing agent comprising silicon dioxide.
Figure 5B:
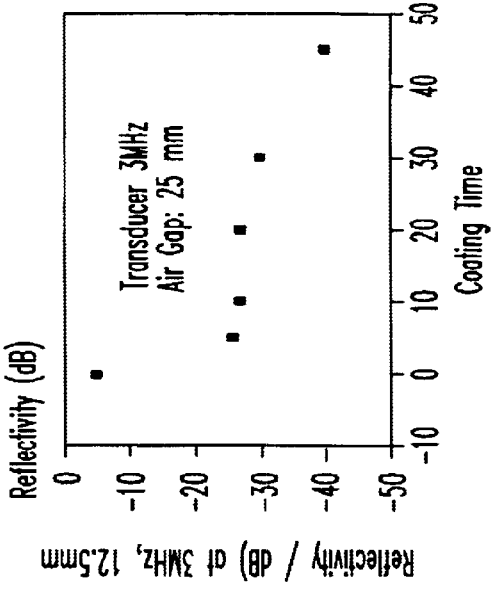
Figure 5C:
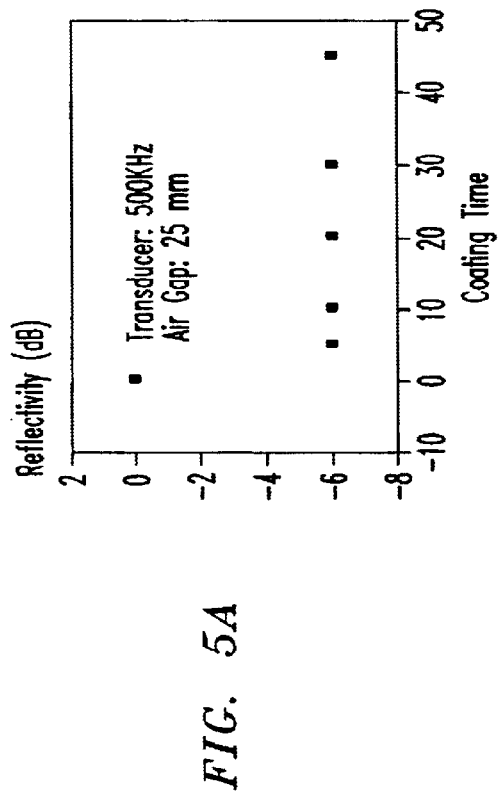
Figure 5D:
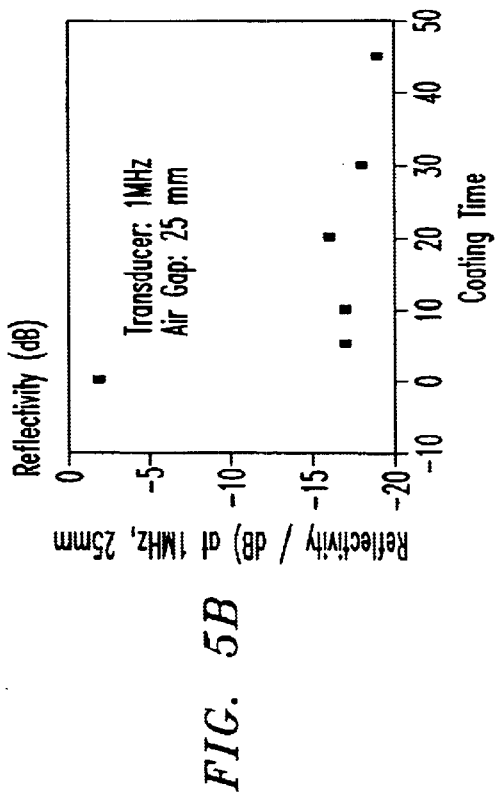

To establish optimal measurement condition, various transducers, each emitting ultrasonic signals at different frequencies, were situated above the coated polishing surface of the pads, with the transducer located at various distances from the surface. As illustrated in FIGS. 5A through 5D, the frequency of the transmitted ultrasonic signal and the air gap between the polishing surface and the transducer are important parameters affecting the relative amounts of reflectivity observed. For example, the reflectance from transmitted signals of ~500 KHz and ~1 MHz were relatively insensitive to the period of coating, as compared to transmitted signals at ~2 MHz and ~3 MHz. As illustrated in FIGS. 5C and 5D, the air gap between the transducer and the polishing surface also affected the reflectance signal. As illustrated in FIG. 5D, using a transmitted signal with a frequency of ~3 MHz and an air gap of ~12.5 mm, the coating of the polishing surface can be advantageously monitored.

Figure 6:
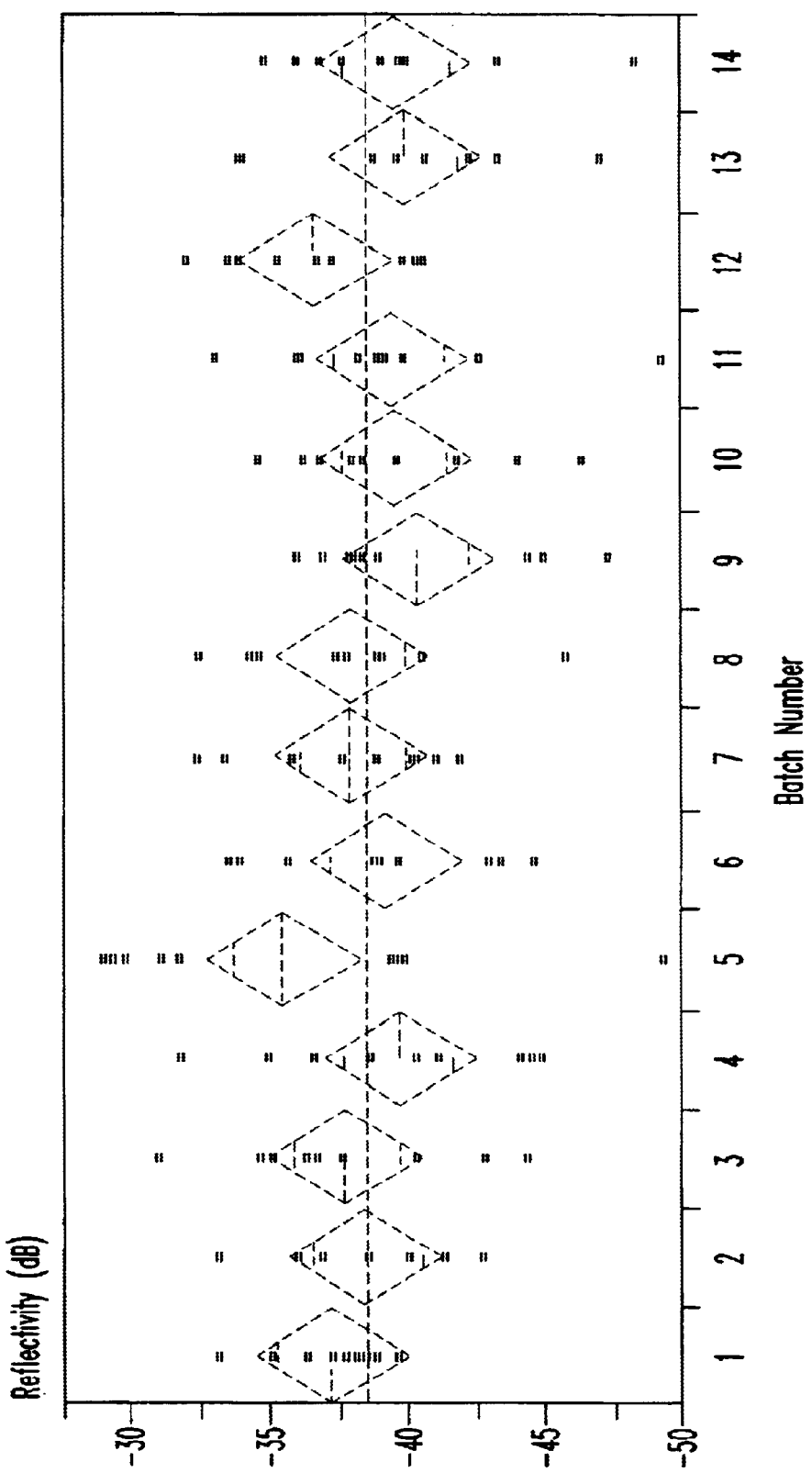
FIG. 6 illustrates the use of noncontact ultrasound to monitor within batch reflectance uniformity of representative polishing pads after coating with tetraisopropyl-titanate.
Figure 7:
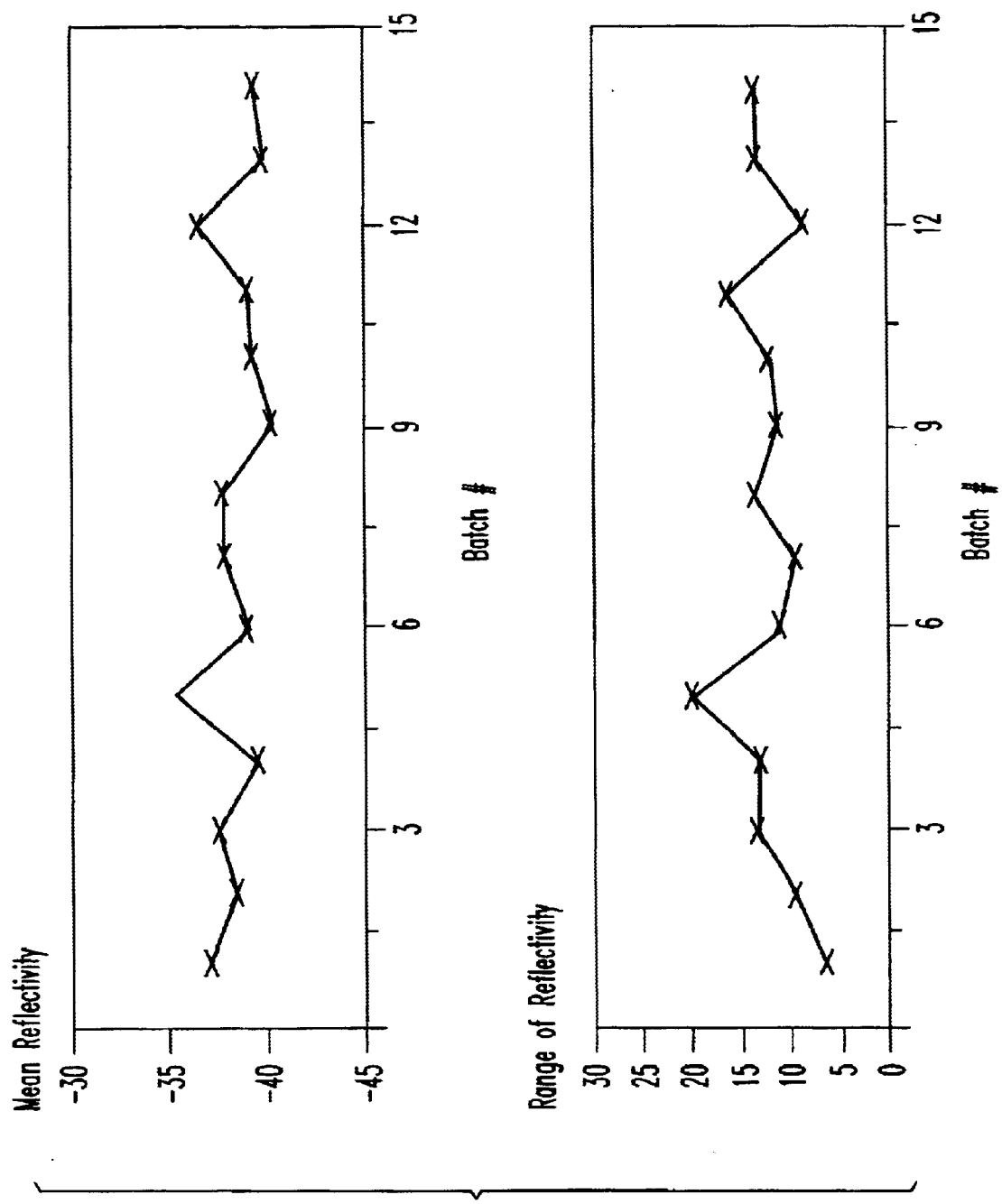
FIG. 7 illustrates the mean reflectance and absolute value of the range of reflectance values of representative polishing pads after coating with tetraisopropyl-titanate.

FIGS. 6 and 7 illustrate the use of noncontact ultrasound to monitor within batch reflectance uniformity of representative polishing pads after coating with a polishing agent. Multiple batches of polishing pads, with several pads per batch, were fabricated similar to that described above using a substrate comprised of a crosslinked polyethylene foam (Product Number SV4M, Volara® from Voltek, Lawrence, Mass.) and a polishing agent comprised of tetraisopropyl-titanate (TYZOR® TPT). FIG. 6 shows the variation in reflectivity obtained from individual polishing pads within each batch. FIG. 7 shows the mean reflectance and absolute value of the range of reflectance values of representative polishing pads after coating with tetraisopropyl-titanate.

Experiment 2

Figure 8:
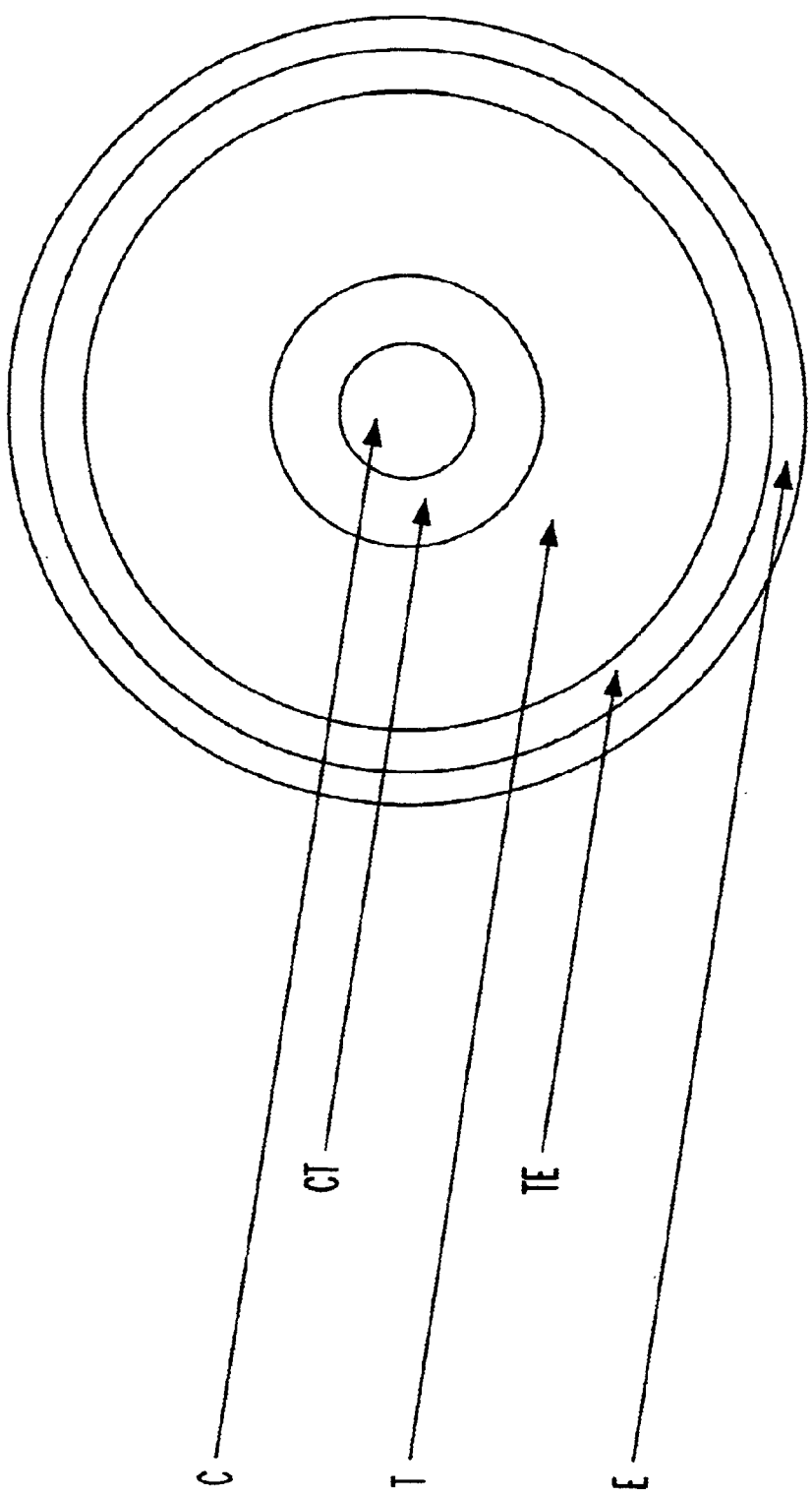
FIG. 8 defines wear sections for a used polishing pad.

To examine wearing patterns of polishing surfaces after various periods of use, polishing pads were prepared by exposing skived J60 thermoplastic foam substrates to the above-described grafting process to produce $SiO_2$ coated polishing pads, designated as "J60SE." As illustrated in FIG. 8, to facilitate comparisons between conventional measurements and the noncontact ultrasonic measurements of the present invention, different sections of the polishing pad were defined as: center (C); center to track (CT); track (T); Track to edge (TE) and Edge (E).

The J60SE polishing pads were subjected to a wearing period by polishing wafers having a deposited about 4000 Å tungsten surface and an underlying about 250 Å thick tantalum barrier layer. Tungsten polishing properties were assessed using a commercial polisher (Product No. EP0222 from Ebara Technologies, Sacramento, Calif.). Unless otherwise noted, the removal rate of tungsten polishing was assessed using a down force of about 13. N per $inch^2$ of substrate(about 3 to about 4 psi); table speed of about 100 to about 250 rpm and a conventional slurry (Product Number MSW2000, from Rodel, Newark Del.). Plasma Enhanced Tetraethylorthosilicate (PE-TEOS) wafers, having a thickness of about 10,000 Å and a deposited tungsten surface having a thickness of about 8,000 Å and an underlying titanium barrier layer having a thickness of about 250 Å, were used for test polishing. A conventional slurry (Product Number MSW2000, from Rodel, Newark Del.) adjusted to a pH of about 2 was used. After polishing, the pads were divided into the above-defined sections for conventional analysis, or the intact pads were analyzed using the noncontact ultrasound system and methods of the present invention.

Figure 9:
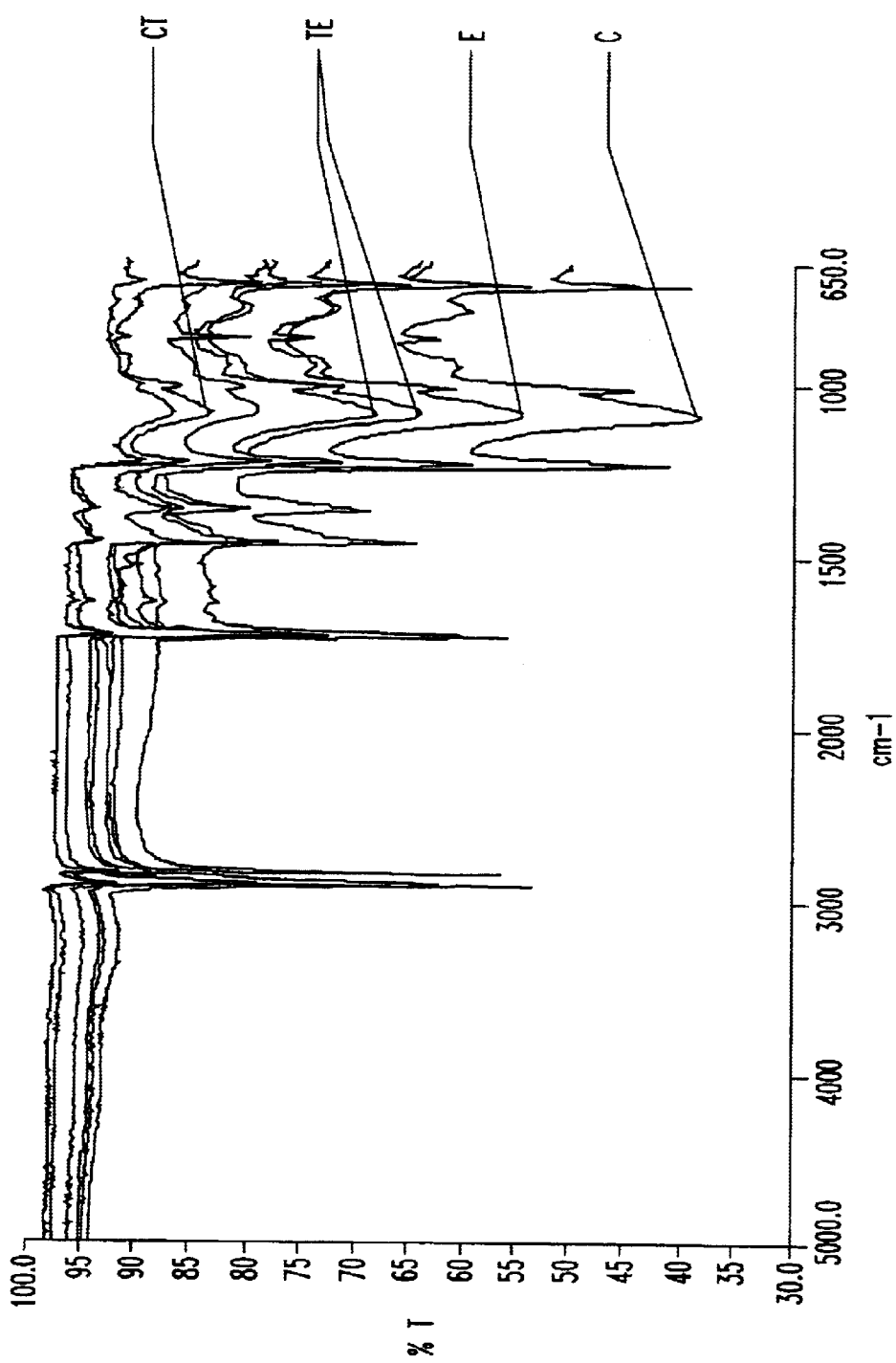
FIG. 9 presents representative near infrared spectra obtained for different sections of a polishing pad after a period of use.

FIG. 9 illustrates conventionally FTIR spectroscopy, obtained using similar procedures to that described in Experiment 1, from different sections of the pad. Sections of the pad corresponding to the center (C) and edge (E) had the largest FTIR spectroscopy signal at about 1010 $cm^{-1}$, signifying the continued presence of $SiO_2$. In contrast, the FTIR spectra from pad material corresponding to the track (T) had a smaller signal at about 1010 $cm^{-1}$.

Figure 10:
FIG. 10 presents representative scanning electron microscopy images of a surface of different sections of a polishing pad after a period of use.
Figure 10:

FIG. 10 show representative conventional Scanning Electron Microscopy Images (SEM) at 100X magnification of the surface of different sections of a polishing pad after a period of use. SEM images were obtained from a commercial instrument (JEOL, Peabody, Mass.). The images illustrate the evolution of changes in the cell structure of the foam. While the cells in the center and edge of the pad appear intact, those around the track defined between the locus of the wafer during polishing were deformed and sheared.

Figure 11:
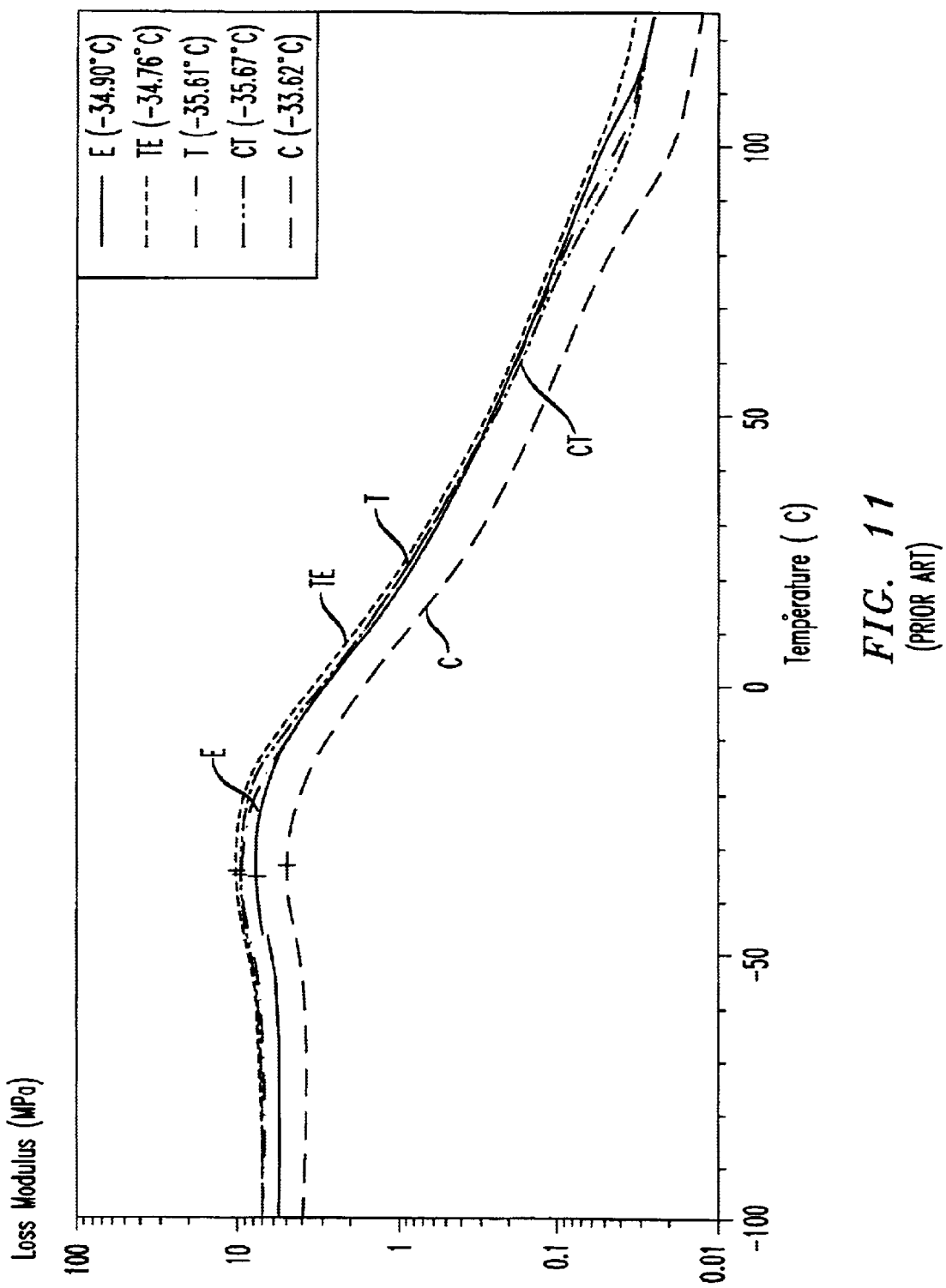
FIG. 11 illustrates the Dynamic Mechanical Analysis showing the relationship between Loss Modulus and Temperature for different sections of a used polishing pad.
Figure 12:
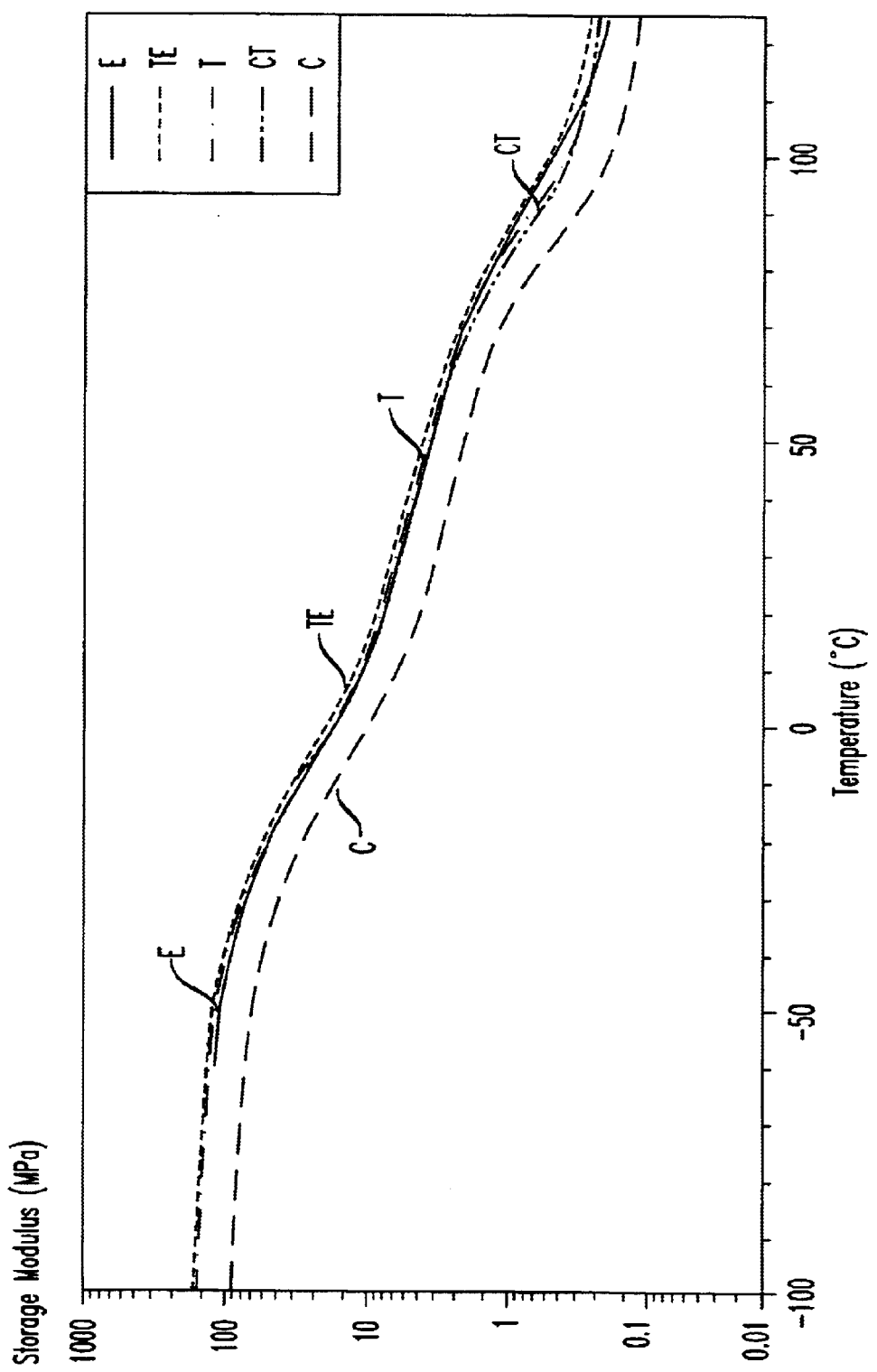
FIG. 12 illustrates the relationship between Storage Modulus and Temperature for different sections of a used polishing pad.
Figure 13:
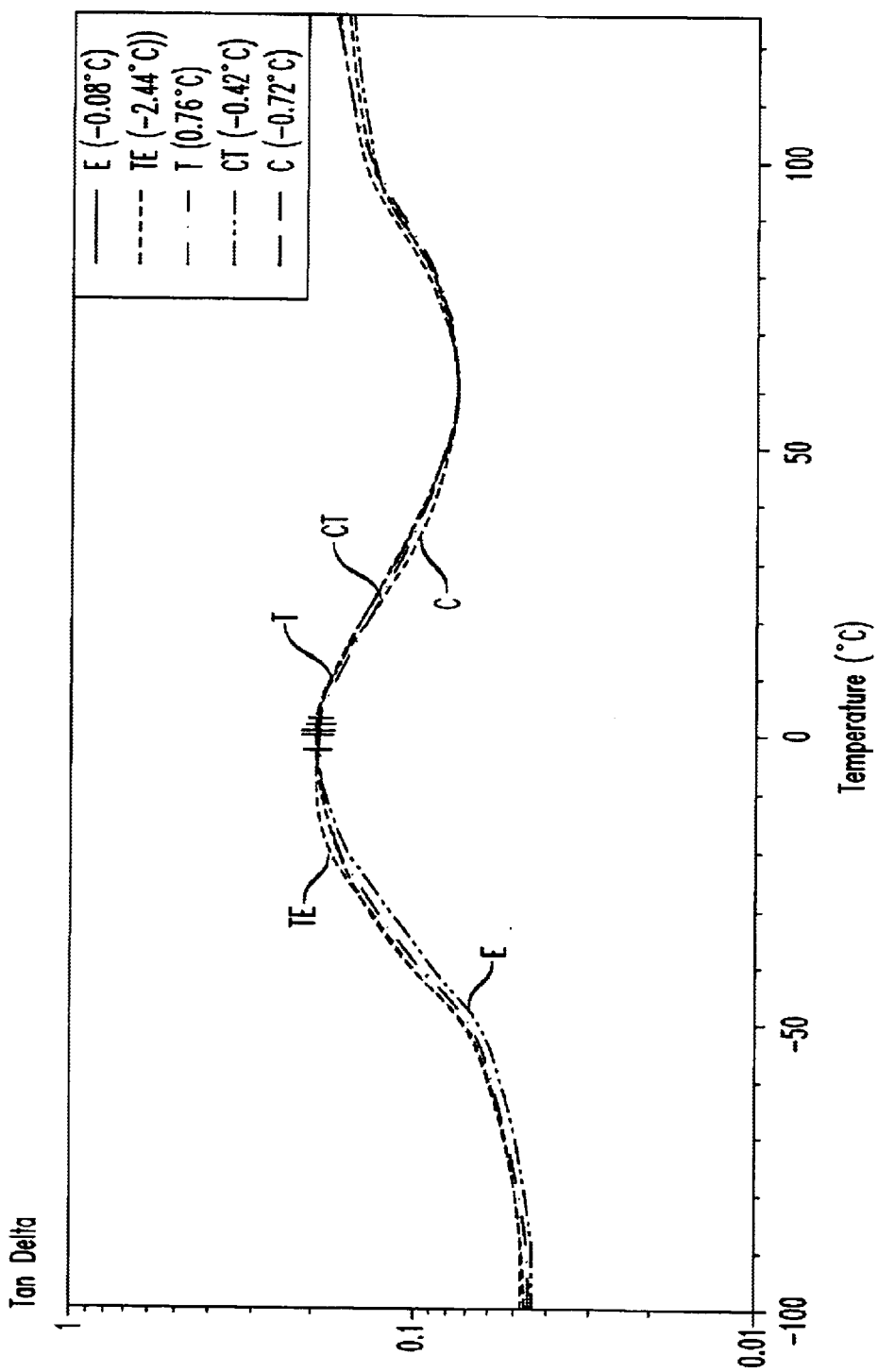
FIG. 13 illustrates the relationship between Tan Delta and Temperature for different sections of a used polishing pad.

The mechanical properties of different sections of J60SE polishing pads after use were assessed using Dynamic Mechanical Analysis (DMA). The DMA measurements were obtained using a commercial instrument and analyzed using Universal V2.5H software (both from TA Instruments, New Castle, Del.). Exemplary data of Storage Modulus, Loss Modulus and Tan Delta are presented in FIGS. 11, 12 and 13, respectively. For FIGS. 11 and 13, maxima are depicted by vertical lines, and temperature at the maximum is presented in the legend. These data illustrate that DMA is relatively insensitive to detecting small changes in the viscoelastic properties of different sections of used pads.

Figure 14:
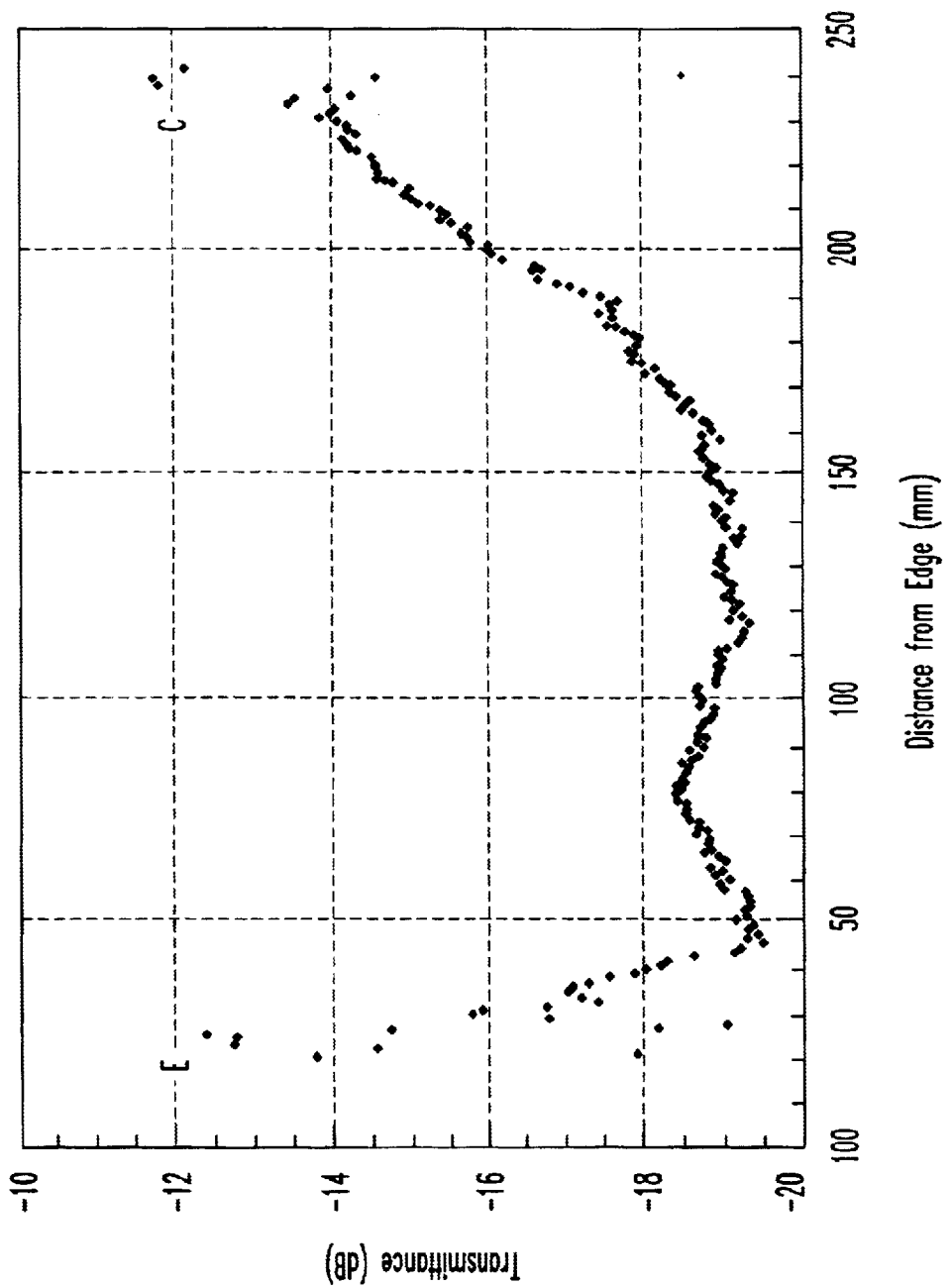
FIG. 14 illustrates the relationship between noncontact ultrasonic transmittance and polishing surface location, as defined by distance from the outer edge to the center of a used polishing.
Figure 15:
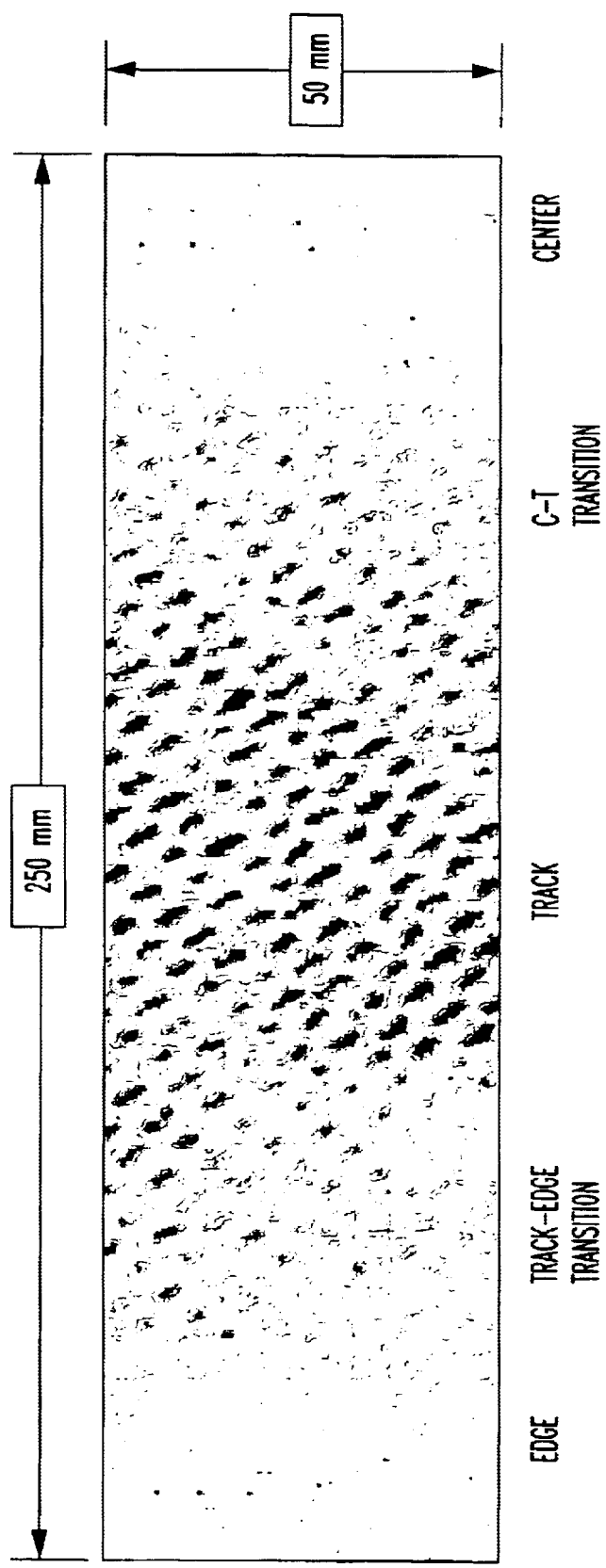
FIG. 15 presents a representative reflectance image of a section of a used polishing pad.

In comparison, non-contact ultrasound measurements shown marked differences between the different sections of used polishing pads. FIG. 14 illustrates the relationship between noncontact ultrasonic transmittance and polishing surface location, as defined by distance from the outer edge to the center of a used polishing pad. The pad edge (E) and center (C) having the least amount of wear also had the highest transmittance, as compared to more central portions of pad having more extensive wear. FIG. 15 illustrates that noncontact ultrasound measurements may be rasterized to produce a reflectance image of a section of the polishing surface of a used polishing pad.

Although the present invention has been described in detail, those skilled in the art should understand that they can make various changes, substitutions and alterations herein without departing from the scope of the invention.

What is claimed is:

1. A method for measuring the surface properties of a polishing pad, comprising:
    situating an ultrasonic probe above a polishing surface of a polishing pad, without contacting said polishing surface;
    transmitting an ultrasonic signal from said probe to said polishing surface, said ultrasonic signal being modified by said polishing surface; and
    receiving said modified signal by said ultrasonic probe,
    wherein said modified signal is a reflected signal used to calculate an acoustic reflectance spectrum of said polishing surface.

2. The method as recited in claim 1, wherein said modified signal is a reflected signal received during coating of a polishing agent onto said polishing surface of a thermoplastic foam substrate.

3. The method as recited in claim 2, wherein said probe and said polishing pad are located in a reaction chamber used for said coating.

4. The method as recited in claim 3, wherein said coating comprises:
    exposing a surface of said thermoplastic foam substrate to an initial plasma reactant to produce a modified surface thereon; and
    exposing said modified surface to a secondary plasma reactant to create said polishing surface on said modified surface, said polishing surface comprised of said polishing agent.

5. The method as recited in claim 2, wherein said coating includes exposing a plastic substrate to a polishing agent dissolved in a supercritical fluid to thereby produce a modified plastic.

6. The method as recited in claim 1, wherein said polishing pad and said probe are coupled to a polishing apparatus comprised of a mechanically driven carrier head and a polishing platen.

7. The method as recited in claim 6, wherein said polishing pad is attached to said polishing platen and said transmitting and said receiving are carried out while said carrier head holds a wafer and imparts a polishing force against said polishing pad to polish a wafer.

8. The method as recited in claim 1, wherein said reflected signal is used to determine an acoustic reflectance image of said polishing surface.

9. A method for measuring the surface properties of a polishing pad, comprising:
    situating an ultrasonic probe above a polishing surface of a polishing pad, without contacting said polishing surface;
    transmitting an ultrasonic signal from said probe to said polishing surface, said ultrasonic signal being modified by said polishing surface; and
    receiving said modified signal by said ultrasonic probe,
    wherein said modified signal is a transmission signal used to determine a relative density of said polishing surface.

10. The method as recited in claim 9, wherein said transmittance signal is used to determine a surface texture of said polishing surface.

* * * * *